United States Patent [19]

Hamersma et al.

[11] Patent Number: 5,741,786
[45] Date of Patent: Apr. 21, 1998

[54] STEROIDS WITH A 17-SPIROMETHYLENE LACTONE OR LACTOL GROUP

[75] Inventors: Johannes Antonius Maria Hamersma; Jaap van der Louw, both of Oss, Netherlands

[73] Assignee: Akzo Nobel N.V., Arnhem, Netherlands

[21] Appl. No.: 547,176

[22] Filed: Oct. 24, 1995

[30] Foreign Application Priority Data

Oct. 27, 1994 [EP] European Pat. Off. ............ 94203117

[51] Int. Cl.$^6$ .................. A61K 31/58; A61K 31/585; C07J 43/00; C07J 21/00
[52] U.S. Cl. ............................... 514/173; 540/28
[58] Field of Search ........................... 540/28; 514/173

[56] References Cited

U.S. PATENT DOCUMENTS 2,875,199  2/1959  Cella et al. ............... 260/239.57
3,657,226  4/1972  LeFevre et al. ........... 260/239.55

FOREIGN PATENT DOCUMENTS 0321010  6/1989  European Pat. Off. .
0558416  9/1993  European Pat. Off. .

OTHER PUBLICATIONS

Drug Evaluations, Annual 1993, pp. 2031–2032, 1991.

*Primary Examiner*—Mukund J. Shah
*Assistant Examiner*—Bruck Kifle
*Attorney, Agent, or Firm*—Mary E. Gormley

[57] ABSTRACT

A steroid with a 17-spiromethylene lactone group having formula I

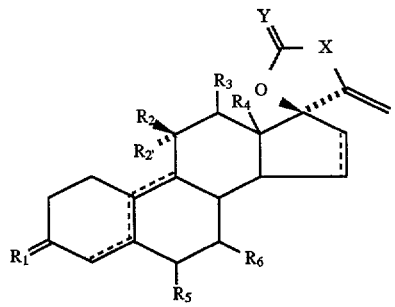

wherein $R_1$ is O, (H,H), (H,OR), or NOR, R being selected from H, (1–6C) alkyl and (1–6C) acyl; $R_2$ is H, (1–6C) alkyl optionally substituted by a halogen, (2–6C) alkenyl optionally substituted by a halogen, (2–6C) alkynyl optionally substituted by a halogen, or halogen; $R_2'$ is H; or $R_2'$ together with $R_2$ is a (1–6C) alkylidene group or a (2–6C) alkenylidene group; or $R_2'$ together with $R_3$ is a bond; $R_3$ is H if not together with $R_2'$ a bond; $R_4$ is (1–6C) alkyl; one of $R_5$ and $R_6$ is hydrogen and the other is hydrogen or (1–6C) alkyl; X is $(CH_2)_n$ or $(C_nH_{2n-2})$ wherein n is 2 or 3, which is optionally substituted with hydroxy, halogen, (1–6C) alkyl, (1–6C) acyl, (7–9C) phenylalkyl, the phenyl group of which may be substituted with (1–6C) alkyl, (1–6C) alkoxy, hydroxy or halogen; Y is O or (H,OH); and the dotted lines indicate optional bonds, at least one of bonds 4–5, 5–10, and 9–10 being a double bond.

The steroids of the invention have progestational activity and can be used as contraceptives.

11 Claims, No Drawings

STEROIDS WITH A 17-SPIROMETHYLENE LACTONE OR LACTOL GROUP

FIELD OF THE INVENTION

The invention relates to steroids with a 17-spiromethylene lactone or lactol group, to their preparation, to a pharmaceutical composition comprising the same, and to their use for the manufacture of a contraceptive.

BACKGROUND OF THE INVENTION

Steroids with a 17-spiromethylene lactone group are known in the art, i.e. as disclosed in EP-A-558,416. Such steroids may have various hormonal activities, which can be assessed by their binding affinity to various receptors. Receptor binding studies have been performed for the 17-spiromethylene lactone steroids of EP-A-558,416 to demonstrate their hormonal activity. These steroids show remarkable antiglucocorticoid and antiprogestogenic activity, and may further have androgenic or anti-androgenic, glucocorticoid and progestogenic properties. It has further been demonstrated that these steroids have a higher binding affinity to the glucocorticoid receptor than to the progesterone receptor, and because of such dissociation, they are claimed to be selective antiglucocorticoid steroids. The steroids of EP-A-558,416 have a 5-membered 17-spiromethylene lactone group, the methylene group of which is juxtapositioned to the carbonyl group.

For many therapeutic applications the glucocorticoid activity, however, is considered to be an unwanted side-effect, and there is then a need for steroids which are selective progestogenic compounds with weak or non-existing glucocorticoid activity.

SUMMARY OF THE INVENTION

Novel 17-spiromethylene lactone and lactol steroids have now been found possessing the desired receptor affinity, which is relatively higher for the progesterone receptor than for the glucocorticoid receptor. These novel steroids thus show selective progesterone receptor binding affinity. Their progesterone receptor binding affinity, moreover, is much higher than that of known structurally related steroids. They are structurally different from the known 17-spiromethylene lactone steroids in that they have a 6- or 7-membered spirolactone or lactol group, whereas the methylene group is separated from the carbonyl (or hydroxymethylene) group by two or three methylene groups. Surprisingly, these steroids show very weak glucocorticoid or antiglucocorticoid activity.

Because of their selectivity, the steroids of the present invention are very suitable for therapeutic use and side-effects resulting from (anti)glucocorticoid activity are believed to be substantially reduced.

DETAILED DESCRIPTION OF THE INVENTION

The steroids of the invention are steroids with a 17-spiromethylene lactone or lactol group, having formula I

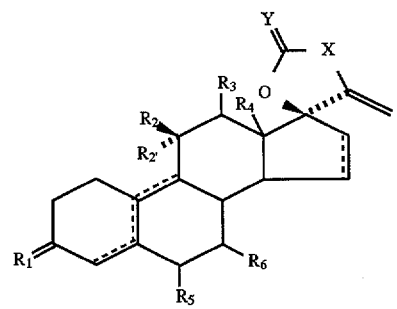

wherein $R_1$ is O, (H,H), (H,OR), or NOR, R being selected from H, (1–6C) alkyl and (1–6C) acyl; $R_2$ is H, (1–6C) alkyl optionally substituted by a halogen, (2–6C) alkenyl optionally substituted by a halogen, (2–6C) alkynyl optionally substituted by a halogen, or halogen; $R_2'$ is H; or $R_2'$ together with $R_2$ is a (1–6C) alkylidene group or (2–6C) alkenylidene group; or $R_2'$ together with $R_3$ is a bond; $R_3$ is H, if not together with $R_2'$ a bond; $R_4$ is (1–6C) alkyl; X is $(CH_2)_n$ or $(C_nH_{2n-2})$ wherein n is 2 or 3, which is optionally substituted with hydroxy, halogen, (1–6C) alkyl, (1–6C) acyl, (7–9C) phenylalkyl, the phenyl group of which may be substituted with (1–6C) alkyl, (1–6C) alkoxy, hydroxy or halogen; one of $R_5$ and $R_6$ is hydrogen and the other is hydrogen or (1–6C) alkyl; Y is O or (H,OH); and the dotted lines indicate optional bonds, at least one of bonds 4–5, 5–10, and 9–10 being a double bond.

17-Spiromethylene lactone steroids of formula I wherein $R_1$ is O, $R_4$ is methyl, Y is O, and n is 2, are preferred.

More preferred are the steroids of formula I wherein $R_1$ is O, $R_2$ is (1–6C) alkyl or (2–6C) alkynyl, $R_2'$ and $R_3$ are H, $R_4$ is methyl, $R_5$ and $R_6$ are hydrogen; X is $(CH_2)_2$, Y is O, and the dotted line in the D-ring is not a bond and the other dotted line is a 4–5 bond.

The most preferred 17-spiromethylene lactone steroids are (11β,17α)-11-ethyl-17-hydroxy-3-oxo-19-norchola-4,20-dien-24-oic acid δ-lactone and (11β,17α)-17-hydroxy-3-oxo-11-(1-propynyl)-19-norchola-4,20-dien-24-oic acid δ-lactone.

The term (1–6C) alkyl means a branched or unbranched alkyl group having 1–6 carbon atoms, such as methyl, ethyl, propyl, isopropyl, butyl, tert-butyl, pentyl, hexyl and the like. Preferred alkyl groups have 1–4 carbon atoms, and most preferred alkyl groups are ethyl and methyl.

The term (2–6C) alkenyl means a branched or unbranched alkenyl group having at least one double bond and 2–6 carbon atoms. Preferred alkenyl groups have 2–4 carbon atoms, such as vinyl and propenyl.

The term (2–6C) alkynyl means a branched or unbranched alkynyl group having at least one triple bond and 2–6 carbon atoms. Preferred alkynyl groups have 2–4 carbon atoms. Examples are ethynyl and 1-propynyl.

The term (1–6C) alkylidene means a branched or unbranched alkylidene group having 1–6 carbon atoms. Preferred alkylidene groups have 1–4 carbon atoms, and most preferred is methylene.

The term (2–6C) alkenylidene means a branched or unbranched alkenylidene group having 2–6 carbon atoms. Preferred alkenylidene groups have 2–4 carbon atoms, such as ethenylidene.

The term (1–6C) acyl means an acyl group derived from an aliphatic carboxylic acid having 1–6 carbon atoms. Acetyl is the most preferred acyl group.

The term halogen means fluorine, chlorine, bromine or iodine. Chlorine is the preferred halogen.

The progestogenic steroids of this invention can be used as contraceptives in mammals, more particularly in humans and animals. The compounds of the invention further exhibit the usual activities known for progestogens. For example, they can be used to treat menstrual disorders and hormone-dependent tumors and they can also be applied in hormone replacement therapy.

The steroids of formula I may be prepared according to well-known methods described and used for the preparation of analogous steroids.

A suitable process for the preparation of some of the steroids of the invention is characterized in that a compound having formula II

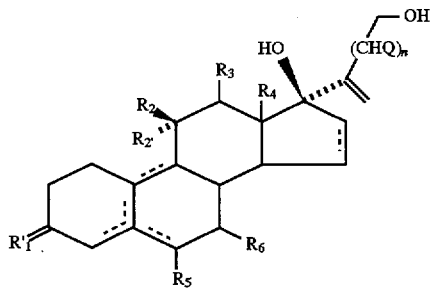

wherein $R_1'$ is O,(H,H) or (H,OR), R being selected from H, (1-6C) alkyl and (1-6C) acyl, or a protected derivative thereof; $R_2$ is H, (1-6C) alkyl optionally substituted by a halogen, (2-6C) alkenyl optionally substituted by a halogen, (2-6C) alkynyl optionally substituted by a halogen, or halogen; $R_2'$ is H; or $R_2'$ together with $R_2$ is a (1-6C) alkylidene group or a (2-6C) alkenylidene group; or $R_2'$ together with $R_3$ is a bond; $R_3$ is H if not together with $R_2'$ a bond; $R_4$ is (1-6C) alkyl; one of $R_5$ and $R_6$ is hydrogen and the other is hydrogen or (1-6C) alkyl; each Q is independently selected from H, (1-6C) alkyl and (7-9C) phenylalkyl, the phenyl group of which may be substituted with (1-6C) alkyl, (1-6C) alkoxy, hydroxy or halogen; n is 2 or 3; and the dotted lines indicate optional bonds, at least one of bonds 4-5, 5-6, 5-10, and 9-10 being a double bond, is converted by oxidation into a steroid with a 17-spiromethylene lactone group and optionally reduced into a compound wherein Y is (H,OH), after which the optionally present protective group is removed, optionally followed by conversion of a compound with formula I wherein $R_1$ is O into the corresponding compound wherein $R_1$ is NOR, R having the meaning as previously defined.

Compounds of formula II can be prepared from the corresponding 17-keto steroids. These 17-keto steroids can be obtained according to the process as disclosed in DE 2,805,490, or as described in Van den Broek et al., Steroids Vol. 30, 481-510 (1977). When said 17-keto steroids are condensed with a 2-metallated-5-(protected hydroxy)-1-pentene or with a 2-metallated-6-(protected hydroxy)-1-hexene, for example with 2-lithio-5-trimethylsilyloxy-1-pentene or with 2-lithio-6-trimethylsilyloxy-1-hexene, followed by removal of the protective group(s), the compounds of formula II are obtained.

Suitable protective groups are known in the art, for example from T. W. Green: Protective Groups in Organic Synthesis (Wiley, NY, 1981).

The addition can also be performed with a suitably protected carboxylic acid derivative, e.g. an ortho ester, or with a suitably protected aldehyde, e.g. 4,5-dihydro-2-(3'-lithiobut-3'-en-1'-yl)-1,3-dioxolane. Alternatively, a metal salt of the alcohol can be used, i.e. no protecting group is present. For the metallation, metals or techniques known in metallo-organic chemistry (e.g. lithium, zinc, magnesium, cerium) can be employed, and also aromatic radical-anion compounds such as lithium naphthalenide. The activating group on the alkene moiety can be a halogen, like bromine or iodine, or a substituted metal, such as a trialkyltin or trialkylgermanium group. The intermediates thus obtained can also be prepared by treatment of suitably protected derivatives of 17,24-dihydroxy-21-norcholan-20-ones with reagents capable of converting a carbonyl group to an alkylidene group, such as Wittig, Horner, Peterson or similar reagents known in the art.

As protecting group for the 3-ketone function cyclic acetals are particularly useful, e.g. 1,2-ethanediyl acetal, 2,2-dimethylpropane-1,3-diyl acetal, or acyclic acetals or thioacetals. Similar groups known in the art, e.g. enol ethers, can also be employed. The conversion of 17,24-dihydroxycholanes to the δ lactones of the invention or of 17,25-dihydroxy-26,27-dinorcholestanes to ε lactones of the invention can be carried out with oxidizing agents known in the art, such as chromium(VI)oxide and silver carbonate on celite. In many cases, the order in which the reactions are performed can be changed, e.g. oxidation of a 17,24-diol to a lactone can be performed prior to the deprotection of the carbonyl group at C-3. Lactols (Y is H,OH) can be prepared by partial oxidation of a compound of formula II by methods known in the art, for instance by a Swern oxidation.

The expression protected OH means a hydroxy group which is protected in a manner as usual for the protection of hydroxy groups, for example as disclosed in T. W. Green.

Alternatively the steroids of the invention can be prepared from compounds of formula III

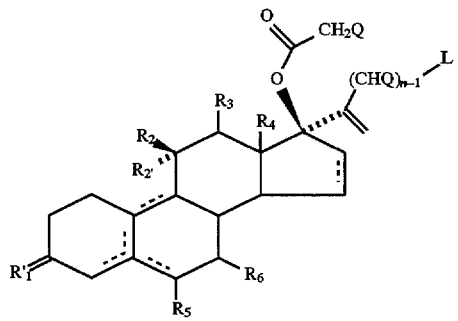

wherein $R_1'$, $R_2$, $R_2'$, $R_3$, $R_4$, $R_5$, $R_6$, n, Q, and the dotted lines have the meanings as given for the compounds of formula II, and L is a leaving group, is converted by base-catalyzed ring-closure into a steroid with a 17-spiromethylene lactone group, optionally followed by alkylation, phenylalkylation, acylation, halogenation optionally followed by dehydrohalogenation, and/or reduced into a compound wherein Y is (H,OH), after which the optionally present protective group is removed, optionally followed by conversion of a compound with formula I wherein $R_1$ is O into the corresponding compound wherein $R_1$ is NOR, as previously defined.

The base-catalyzed ring closure can be performed by sodium or potassium bis(trimethylsilyl)amide or other hindered bases, preferably in an ether, for instance tetrahydrofuran and the like.

Compounds of formula III can be prepared from the corresponding 17-keto steroids. These 17-keto steroids can be obtained according to the process as disclosed in DE 2,805,490, or as described in Van den Broek et al., Steroids Vol. 30, 481–510 (1977). When said 17-keto steroids are condensed with a 2-metallated-3,3-dialkoxy-1-propene or a 2-metallated-4,4-dialkoxy-1-butene, for instance with 2-lithio-3,3-diethoxy-1-propene or 2-lithio-4,4-diethoxy-1-butene, followed by selective hydrolysis of the dialkyl acetal function and reduction of the resulting aldehyde, 17-hydroxy-20-(hydroxymethyl)pregn-20-ene or 17,23-dihydroxy-19,24-dinorchol-20-ene derivatives can be prepared. The 17-hydroxy group is esterified into a suitable ester, for instance an acetate. The other hydroxy group is converted to a leaving group, for example by reaction with tosyl chloride to give a tosylate.

Suitable leaving groups are known in the art, for example from A. L. Ternay: Contemporary Organic Chemistry (2nd ed., W. B. Saunders Company, 1979, see pages 158 and 170–172). Preferred leaving groups are halogens such as chlorine, bromine, and iodine, and in particular the tosyloxy group.

Alkylation and phenylalkylation can be performed by methods known in the art, for instance by using lithium diisopropylamide (LDA) or potassium bis(trimethylsilyl)-amide and the like.

For the preparation of 2-metallated dialkoxyalkenes from alkenylhalogenides, metals or techniques known in metalloorganic chemistry, such as alkyllithium and the ones described above, can be used. As protecting group for the aldehyde function above-mentioned cyclic acetals and acyclic acetals, e.g. dimethyl acetals or thioacetals, or similar groups known in the art, can be employed. Again, the activating group on the alkene moiety can be an halogen, like bromine or iodine, or a substituted metal, such as a trialkyltin or trialkylgermanium group.

The synthesis of 17-hydroxy-20-(hydroxymethyl)pregn-20-enes can also be achieved by addition of suitably protected 2-metallo-2-propen-1-ols to estran-17-ones, followed by deprotection of the hydroxy group. The conversion of 17-hydroxy-20-(hydroxymethyl)pregn-20-enes to the corresponding 17-mono-acetates or 17-mono-propionates can be accomplished using acidic catalysts, e.g. phosphorus oxychloride or oxalic acid in trialkyl orthoacetate or trialkyl orthopropionate. Some of the lactones of this invention can also be prepared by selective reduction of 17-hydroxychola-20,22-dien-24-oic acid δ lactones. Alternatively, they can be prepared by reductive dehalogenation of e.g. 21-, 22- or 23-bromo derivatives of the former lactones, or by analogous removal of similar substituents amenable to reduction, e.g. [(4-methylphenyl)sulfonyloxy] groups. Similar procedures can be used to produce ε lactones by reduction of halogenated and/or unsaturated 17-hydroxy-chol-20-ene-24-carboxylic acid ε lactones. The lactones of the invention can also be prepared by lactonisation of a 17-hydroxycholan-24-oic acid, or by lactonisation of an ester of such an acid (e.g. an acetate, a t-butyl, or a trialkylsilyl ester). They can also be prepared from a 17-hydroxy-24-norchola-23,23-dicarboxylic acid, or from mono- or di-esters of such an acid, or from 17-hydroxycholano-24-nitriles or a 23-cyano-17-hydroxycholan-24-oic acid or esters thereof. The ε lactones can also be prepared by a similar procedure from a 17-hydroxycholane-24-carboxylic acid or from an ester of such an acid, or they can be prepared from a 17-hydroxycholane-24,24-dicarboxylic acid or from mono- or di-esters of such an acid, or be prepared from 17-hydroxycholane-24-carbonitriles or from 24-cyano-17-hydroxycholane-24-carboxylic acids or esters thereof.

The steroids of formula I wherein n=2 and Y is O can also be prepared by oxidation of a hemiacetal (a lactol of the invention) of the aldehyde analogues of the compounds of formula II having a 24-oxo group.

The compounds of the invention may be administered enterally or parenterally, and for humans preferably in a daily dosage of 0,0001–10 mg per kg body weight. Mixed with pharmaceutically suitable auxiliaries, e.g. as described in the standard reference, Gennaro et al., Remington's Pharmaceutical Sciences (18th ed., Mack Publishing Company, 1990, see especially Part 8: Pharmaceutical Preparations and Their Manufacture), the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray. For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

EXAMPLE 1

(17α)-17-Hydroxy-3-oxo-19-norchola-4,20-dien-24-oic acid δ lactone was prepared from 3-ethoxyestra-3,5-dien-17-one as follows:

i)—A solution of 16.6 g of 2-bromo-5-trimethylsilyloxy-1-pentene in 280 ml of dry ether was cooled to −78° C., and 88 ml of a tert-butyllithium solution (1.7M in pentane) were added dropwise. After 15 min, 14.9 g of the steroid mentioned above were added; the mixture was then allowed to warm to 0° C. over a period of 2 h. Subsequently, the reaction mixture was poured into a saturated aqueous solution of ammonium chloride, which was extracted three times with ether. The combined extracts were washed with a solution of sodium hydrogencarbonate and with brine, dried over sodium sulfate, and concentrated under reduced pressure to afford 23 g of the desired (17α)-3-ethoxy-24-trimethylsilyloxy-19-norchola-3,5,20-trien-17-ol, which were used in the subsequent step without further purification.

ii)—A solution of 23 g of the above product in a mixture of 460 ml of acetone and 23 ml of 6N hydrochloric acid was stirred at room temperature for 1.5 h. A saturated aqueous solution of sodium hydrogencarbonate was then added and the acetone was removed under reduced pressure. The residue was extracted three times with ethyl acetate, the combined extracts were washed with brine, dried over sodium sulfate, and concentrated under reduced pressure. The residue was chromatographed to afford 9.07 g of (17α)-17,24-dihydroxy-19-norchola-4,20-dien-3-one.

iii)—To a cooled solution of 2.46 g of the diol obtained in the previous step in a mixture of 35 ml of acetone and 14 ml of water were added dropwise 6.8 ml of an 8N solution of chromium trioxide in sulfuric acid. The reaction mixture was stirred at room temperature for 1 h; it was then poured into a saturated aqueous solution of sodium thiosulfate and the product was extracted into ethyl acetate. The extracts were washed successively with a saturated aqueous solution of sodium thiosulfate, a saturated aqueous solution of sodium hydrogencarbonate, and brine. The solution was dried over sodium sulfate and concentrated under reduced pressure. Column chromatography of the residue afforded 0.66 g of the desired (17α)-17-hydroxy-3-oxo-19-norchola-4,20-dien-24-oic acid δ lactone. M.p. 207.8° C.; $[\alpha]_D^{20}$=-25.5° (c=1, chloroform).

EXAMPLE 2

In a manner similar to Example 1 were prepared:

a) (17α)-13-Ethyl-17-hydroxy-3-oxo-18,19-dinorchola-4,20-dien-24-oic acid δ lactone from 13-ethylgon-5-ene-3,17-dione cyclic 3-(1,2-ethanediyl acetal). M.p. >250° C.; $[\alpha]_D^{20}$=-15.8° (c=1, chloroform).

b) (17α)-17-Hydroxy-11-methylene-3-oxo-19-norchola-4,20-dien-24-oic acid δ lactone from 11-methyleneestr-5-ene-3,17-dione cyclic 3-(1,2-ethanediyl acetal). M.p. 239° C.; $[\alpha]_D^{20}$=+81.2° (c=1, chloroform).

c) (11β,17α)-17-Hydroxy-11-methyl-3-oxo-19-norchola-4,20-dien-24-oic acid δ lactone from (11β)-11-methylestr-5-ene-3,17-dione cyclic 3-(1,2-ethanediyl acetal). M.p 219° C.; $[\alpha]_D^{20}$=+11.9° (c=1, chloroform).

d) (17α)-17-Hydroxy-11-methylene-3-oxo-19-norchola-4,15,20-trien-24-oic acid δ lactone from 11-methyleneestr-5,15-diene-3,17-dione cyclic 3-(1,2-ethanediyl acetal). M.p. 168.5° C.; $[\alpha]_D^{20}$=+50.2° (c=1, chloroform).

e) (11β,17α)-17-Hydroxy-11-methyl-19-norchola-4,20-dien-24-oic acid δ lactone from (11β)-11-methylestr-4-en-17-one. M.p. 184.2° C.; $[\alpha]_D^{20}$=+13.2° (c=1, chloroform).

f) (11β,17α)-11-Chloro-17-hydroxy-3-oxo-19-norchola-4,20-dien-24-oic acid δ lactone from (11β)-11-chloroestr-5-ene-3,17-dione cyclic 3-(1,2-ethanediyl acetal). M.p. 192.8° C.; $[\alpha]_D^{20}$=+61.2° (c=1, chloroform).

g) (11β,17α)-11-Ethenyl-17-hydroxy-3-oxo-19-norchola-4,20-dien-24-oic acid δ lactone from (11β)-11-ethenylestr-5-ene-3,17-dione cyclic 3-(1,2-ethanediyl acetal). M.p. 226° C.; $[\alpha]_D^{20}$=+45.2° (c=1, chloroform).

h) (11β,17α)-11-Ethynyl-17-hydroxy-3-oxo-19-norchola-4,20-dien-24-oic acid δ lactone from (11β)-11-ethynylestr-5-ene-3,17-dione cyclic 3-(1,2-ethanediyl acetal). M.p. 213° C.; $[\alpha]_D^{20}$=+39.9° (c=1, dioxane).

i) (11β,17α)-17-Hydroxy-3-oxo-11-(1-propynyl)-19-norchola-4,20-dien-24-oic acid δ lactone from (11β)-11-(1-propynyl)estr-5-ene-3,17-dione cyclic 3-(1,2-ethanediyl acetal). M.p. 147.7° C.; $[\alpha]_D^{20}$=+71.5° (c=1, chloroform).

j) (11β,17α)-17-Hydroxy-3-oxo-11-(2-propenyl)-19-norchola-4,20-dien-24-oic acid δ lactone from (11β)-11-(2-propenyl)estr-5-ene-3,17-dione cyclic 3-(1,2-ethanediyl acetal). M.p. 214° C.; $[\alpha]_D^{20}$=+9° (c=1, chloroform).

k) (17α)-11-Ethenylidene-17-hydroxy-3-oxo-19-norchola-4,20-dien-24-oic acid δ lactone from 11-ethenylidene-estr-5-ene-3,17-dione cyclic 3-(1,2-ethanediyl acetal). M.p. 217° C.; $[\alpha]_D^{20}$=+181.6° (c=1, chloroform).

l) (17α)-17-Hydroxy-3-oxo-19-norchola-4,11,20-trien-24-oic acid δ lactone from estra-5,11-diene-3,17-dione cyclic 3-(1,2-ethanediyl acetal). M.p. 190° C.; $[\alpha]_D^{20}$=+0.9° (c=0.53, chloroform).

m) (6α,17α)-17-Hydroxy-6-methyl-3-oxo-19-norchola-4,20-dien-24-oic acid δ lactone from 6-methylestr-5-ene-3,17-dione cyclic 3-(1,2-ethanediyl acetal). M.p. 196° C.; $[\alpha]_D^{20}$=-61.8° (c=0.5, chloroform).

n) (11β,17α)-11-Chloromethyl-17-hydroxy-3-oxo-19-norchola-4,20-dien-24-oic acid δ lactone from (11β)-11-chloromethylestr-5-ene-3,17-dione cyclic 3-(1,2-ethanediyl acetal). M.p. 198° C.

o) (11β,17α)-11-Ethyl-17-hydroxy-3-oxo-19-norchola-4,20-dien-24-oic acid δ lactone from (11β)-11-ethylestr-5-ene-3,17-dione cyclic 3-(1,2-ethanediyl acetal). M.p. 224° C.; $[\alpha]_D^{20}$=-2.1° (c=1, chloroform).

p) (11β,17α)-11-Ethyl-17-hydroxy-19-norchola-4,20-dien-24-oic acid δ lactone from (11β)-11-ethylestr-4-en-17-one. M.p. 185° C.; $[\alpha]_D^{20}$=-2.6° (c=0.1, chloroform).

EXAMPLE 3

(17α)-17-Hydroxy-11-methylene-3-oxo-19-norchola-4,20-dien-24-oic acid δ lactone (Example 2) was also prepared from (17α)-17,24-dihydroxy-11-methylene-19-norchola-4,20-dien-3-one via a stepwise oxidation process as follows:

i)—Dimethyl sulfoxide (0.96 ml) was added at –60° C. to a solution of 0.761 ml of oxalyl chloride in 30 ml of dry dichloromethane. After 15 min stirring, a solution of 1.11 g of (17α)-17,24-dihydroxy-11-methylene-19-norchola-4,20-dien-3-one in 25 ml of dichloromethane was added dropwise and stirring was continued for 1 h. Triethylamine (6 ml) was added and the reaction mixture was allowed to warm to 0° C. over 30 min. Stirring was continued for another 30 min and the mixture was poured into a saturated aqueous solution of sodium hydrogencarbonate. The product was extracted into ethyl acetate; the extracts were washed with brine, dried over sodium sulfate, and concentrated under reduced pressure. Column chromatography gave 0.50 g of (17α,24Xi)-17-hydroxy-11-methylene-3-oxo-19-norchola-4,20-dien-24-al cyclic 24,17-hemiacetal. M.p. 95° C.

ii)—Pyridinium dichromate (0.66 g) was added to a solution of 0.050 g of the steroid obtained in the previous step in 5 ml of dry dimethyl formamide. After stirring for 1 h at room temperature, the reaction mixture was poured into 100 ml of water. The product was extracted into ethyl acetate; the extracts were washed with water (3 times) and with brine, dried over sodium sulfate, and concentrated under reduced pressure. Column chromatography gave 0.030 g of (17α)-17-hydroxy-11-methylene-3-oxo-19-norchola-4,20-dien-24-oic acid δ lactone.

EXAMPLE 4

(17α)-17-Hydroxy-11-methylene-3-oxo-19-norchola-4,20-dien-24-oic acid δ lactone was also prepared via an alternative route from 11-methyleneestr-5-ene-3,17-dione cyclic 3-(1,2-ethanediyl acetal) as follows:

i)—A solution of 78.38 g of 2-bromo-3,3-diethoxy-propene (see Ber. Dtsch. Chem. Ges. 1898, 31, 1015) in 750 ml of dry THF was cooled to –60° C. and 234 ml of a solution of n-butyllithium (1.6N in hexane) was added dropwise. After 15 min, a solution of 82.0 g of the above steroid in 1000 ml of THF were added dropwise. The temperature was allowed to rise to 0° C. over a period of 2 h after which 500 ml of a saturated aqueous solution of ammonium chloride were added. The product was extracted into ethyl acetate; the extracts were washed with brine, dried over sodium sulfate, and concentrated under reduced pressure. The crude material thus obtained was subjected to the procedure described above for a second time. The resulting 137.6 g of (17α)-3,3-[1,2-ethanediylbis(oxy)]-17-hydroxy-11-methylene-19-norpregna-5,20-diene-20-carboxaldehyde diethyl acetal were used in the subsequent step without further purification.

ii)—130.7 g of the product obtained in the previous step were dissolved in 1307 ml of dry THF. p-Toluenesulfonic acid (7.86 ml of a 1N aqueous solution) was added, and the mixture was stirred at room temperature for 45 min. The reaction mixture was then added dropwise to an ice-cooled suspension of 27 g of lithium aluminium hydride in 1000 ml of THF. After 1 h at 0° C., the reaction was quenched with a saturated aqueous solution of sodium sulfate. Ethyl acetate was added, and the mixture was filtered over celite. The filtrate was washed with a saturated aqueous solution of sodium hydrogencarbonate and with brine, dried over sodium sulfate, and concentrated under reduced pressure. The residue was purified by crystallization to afford 62.7 g of the desired (17α)-17-hydroxy-20-(hydroxymethyl)-11-methylene-19-norpregna-5,20-dien-3-one cyclic 1,2-ethanediyl acetal.

iii)—A solution of 38.6 g of the above diol in a mixture of 200 ml of dry ethyl acetate, 200 ml of trimethyl orthoacetate and 1.0 ml of phosphorus oxychloride was stirred at room temperature for 1 h. The reaction mixture was then diluted with 1000 ml of ethyl acetate; 1000 ml of water were added and stirring was continued for another 30 min. The mixture was poured into a saturated aqueous solution of sodium hydrogencarbonate and the aqueous layer was extracted three times with ethyl acetate. The combined organic phases were washed with brine, dried over sodium sulfate, and concentrated under reduced pressure to afford 47.15 g of (17α)-17-acetoxy-20-(hydroxymethyl)-11-methylene-19-norpregna-5,20-dien-3-one cyclic 1,2-ethanediyl acetal, which were used in the subsequent step without further purification.

iv)—A solution of 47.15 g of the mono-ester obtained in the previous step in 80 ml of dry pyridine was cooled in a water bath. p-Toluenesulfonyl chloride (40 g) was added and the mixture was stirred for 4 h. The mixture was then poured into 2000 ml of water, and the resulting suspension was stirred for 1 h. The product was taken up in ethyl acetate and the aqueous phase was extracted with the same solvent. The combined organic phases were washed with a saturated aqueous solution of sodium hydrogencarbonate and with brine, dried over sodium sulfate, and concentrated under reduced pressure to give 55.0 g of (17α)-17-acetoxy-11-methylene-20-[[[(4-methylphenyl) sulfonyl]oxy]methyl]-19-norpregna-5,20-dien-3-one cyclic 1,2-ethanediyl acetal, which were used in the subsequent step without further purification.

v)—A solution of 60 g of potassium bis(trimethylsilyl) amide in 1500 ml of dry THF was cooled to −30° C. A solution of 55 g of the tosylate obtained in the previous step in 400 ml of THF was added and the mixture was stirred at −30° C. for 30 min. The reaction was quenched by addition of 500 ml of a saturated aqueous solution of ammonium chloride, and the mixture was stirred at room temperature for 15 min. The product was then extracted into ethyl acetate, the extracts were washed with brine, dried over sodium sulfate, and concentrated under reduced pressure. The residue was purified by column chromatography to afford 24.52 g of (17α)-3,3-[1,2-ethanediylbis(oxy)]-17-hydroxy-11-methylene-19-norchola-5,20-dien-24-oic acid δ lactone.

vi)—Following a procedure analogous to that of step ii of Example 1, 5.00 g of the lactone obtained in the previous step were converted to 3.34 g of the desired (17α)-17-hydroxy-11-methylene-3-oxo-19-norchola-4,20-dien-24-oic acid δ lactone.

EXAMPLE 5

In a manner analogous to the procedure of Example 4 the following products were prepared:

a) (17α)-17-Hydroxy-19-norchola-4,20-dien-24-oic acid δ lactone from estr-4-en-17-one. M.p. 176° C.

b) (11β,17α)-17-Hydroxy-11-(1-propynyl)-19-norchola-4,20-dien-24-oic acid δ lactone from (11β)-11-(1-propynyl) estr-4-en-17-one. M.p 212° C.; $[α]_D^{20}$=+13.9° (c=1, chloroform).

c) (7α,17α)-17-Hydroxy-7-methyl-3-oxo-19-norchola-4,20-dien-24-oic acid δ lactone from (7α)-7-methylestr-5(10)-ene-3,17-dione cyclic 3-(1,2-ethanediyl acetal). M.p. 197° C.; $[α]_D^{20}$=0° (c=1, chloroform).

EXAMPLE 6

(17α,23S)-17-Hydroxy-11-methylene-3-oxo-19-norchola-4,20-diene-23-carboxylic acid δ lactone was prepared from (17α)-3,3-[1,2-ethanediylbis(oxy)]-17-hydroxy-11-methylene-19-norchola-5,20-dien-24-oic acid δ lactone (Example 4, step v) as follows:

i)—A solution of 0.506 ml of diisopropylamine in 15 ml of dry THF was cooled to −30° C., and 2.25 ml of an n-butyllithium solution (1.6N in hexane) was added dropwise. The mixture was stirred for 10 min at −10° C. and then cooled to −78° C. A solution of 1.23 g of the steroid mentioned above in 15 ml of THF was added dropwise and stirring was continued for 15 min. Iodomethane (0.93 ml) was added and the mixture was allowed to warm to 0° C. over 2 h. A saturated aqueous solution of ammonium chloride was added and the product was extracted into ethyl acetate. The combined organic phases were washed with brine, dried over sodium sulfate, and concentrated under reduced pressure to afford 1.22 g of (17α,23S)-3,3-[1,2-ethanediylbis(oxy)]-17-hydroxy-11-methylene-19-norchola-5,20-diene-23-carboxylic acid δ lactone, which were used in the following step without further purification.

ii)—Following a procedure analogous to that of step ii of Example 1, 1.22 g of the product of the previous step was converted to 0.67 g of (17α,23S)-17-hydroxy-11-methylene-3-oxo-19-norchola-4,20-diene-23-carboxylic acid δ lactone. M.p. 187° C.; $[α]_D^{20}$=+92° (c=1, chloroform).

EXAMPLE 7

Following a procedure analogous to that described in Example 6, (17α,23S)-17-hydroxy-11-methylene-3-oxo-24-phenyl-19-norchola-4,20-diene-23-carboxylic acid δ lactone was prepared from (17α)-3,3-[1,2-ethanediylbis-(oxy)]-17-hydroxy-11-methylene-19-norchola-5,20-dien-24-oic acid δ lactone (Example 4, step v). M.p. 177° C.; $[α]_D^{20}$=+58.8° (c=1, chloroform).

EXAMPLE 8

(17α,23S)-23-Chloro-17-hydroxy-11-methylene-3-oxo-19-norchola-4,20-dien-24-oic acid δ lactone was prepared from (17α)-3,3-[1,2-ethanediylbis(oxy)]-17-hydroxy-11-methylene-19-norchola-5,20-dien-24-oic acid δ lactone (Example 4, step v) as follows:

i)—A solution of 5.04 ml of diisopropylamine in 75 ml of dry THF was cooled to −30° C., and 22.5 ml of an n-butyllithium solution (1.6N in hexane) was added dropwise. The mixture was stirred for 10 min at −10° C. and then cooled to −78° C. A solution of 12.3 g of the steroid mentioned above in 120 ml of THF was added dropwise and stirring was continued for 15 min. The resulting solution was transferred in 5 min to a solution of 46.2 g of carbon tetrachloride in 150 ml of THF, previously cooled to −78° C. Stirring was continued for 1 h. A saturated aqueous solution of ammonium chloride was added and the product was extracted into ethyl acetate. The combined organic phases were washed with brine, dried over sodium sulfate, and concentrated under reduced pressure affording 6.12 g of (17α,23S)-23,25,25,25-tetrachloro-3,3-[1,2-ethanediylbis(oxy)]-17-hydroxy-11-methylene-19,26, 27-trinorcholesta- 5,20-dien-24-one, 0.24 g of (17α)-23,23-dichloro-3,3-[1,2-ethanediylbis(oxy)]-17-hydroxy-11-methylene-19-norchola-5,20-dien-24-oic acid δ lactone, 0.43 g of (17α,23S)-23-chloro-3,3-[1,2-ethanediylbis(oxy)]-17-hydroxy-11-methylene-19-norchola-5,20-dien-24-oic acid δ lactone, and 0.45 g of (17α,23R)-23-chloro-3,3-[1,2-ethanediylbis(oxy)]-17-hydroxy-11-methylene-19-norchola-5,20-dien-24-oic acid δ lactone.

ii)—A solution of 6.12 g of (17α,23S)-23,25,25,25-tetrachloro-3,3-[1,2-ethanediylbis(oxy)]-17-hydroxy-11-methylene-19,26,27-trinorcholesta-5,20-dien-24-one in 90 ml of toluene and 10 ml of diisopropylethylamine was heated under reflux for 1 h. After cooling, the reaction mixture was poured into a saturated aqueous solution of ammonium chloride. The aqueous layer was extracted with ethyl acetate and the combined organic phases were washed with a saturated aqueous solution of sodium hydrogencarbonate and with brine. Drying over sodium sulfate and evaporation of solvents afforded 4.57 g of (17α,23S)-23-chloro-3,3-[1,2-ethanediylbis(oxy)]-17-hydroxy-11-methylene-19-norchola-5,20-dien-24-oic acid δ lactone, which were used in the following step without further purification.

iii)—Following a procedure analogous to that of step ii of Example 1, 1.00 g of the product of the previous step was converted to 0.67 g of (17α,23S)-23-chloro-17-hydroxy-11-methylene-3-oxo-19-norchola-4,20-dien-24-oic acid δ lactone. M.p. 223° C.; $[\alpha]_D^{20}$=+65.7° (c=1, chloroform).

EXAMPLE 9

(17α,23R)-23-Chloro-17-hydroxy-11-methylene-3-oxo-19-norchola-4,20-dien-24-oic acid δ lactone was prepared from (17α,23R)-23-chloro-3,3-[1,2-ethanediylbis(oxy)]-17-hydroxy-11-methylene-19-norchola-5,20-dien-24-oic acid δ lactone (Example 8, step i) using a procedure analogous to that of step ii of Example 1. M.p 219° C.; $[\alpha]_D^{20}$=+112° (c=1, chloroform).

EXAMPLE 10

(17α)-23,23-Dichloro-17-hydroxy-11-methylene-3-oxo-19-norchola-4,20-dien-24-oic acid δ lactone was prepared from (17α,23S)-23-chloro-3,3-[1,2-ethanediylbis(oxy)]-17-hydroxy-11-methylene-19-norchola-5,20-dien-24-oic acid δ lactone (Example 8, step ii) as follows:

i)—A solution of 1.17 ml of diisopropylamine in 70 ml of dry THF was cooled to −30° C. and 5.16 ml of an n-butyllithium solution (1.6N in hexane) were added dropwise. The mixture was stirred for 10 min at −10° C. and then cooled to −78° C. A solution of 3.06 g of the steroid mentioned above in 25 ml of THF was added dropwise and stirring was continued for 15 min. Carbon tetrachloride (22.32 g) was added in 5 min and the mixture was allowed to warm to 0° C. over 15 min. Stirring was continued for another 15 min; a saturated aqueous solution of ammonium chloride was added and the product was extracted into ethyl acetate. The combined organic phases were washed with brine, dried over sodium sulfate, and concentrated under reduced pressure. Column chromatography of the residual product gave 1.71 g of (17α)-23,23-dichloro-3,3-[1,2-ethanediylbis(oxy)]-17-hydroxy-11-methylene-19-norchola-5,20-dien-24-oic acid δ lactone.

ii)—Following a procedure analogous to that of step ii of Example 1, 0.85 g of the product of the previous step was converted to 0.77 g of (17α)-23,23-dichloro-17-hydroxy-11-methylene-3-oxo-19-norchola-4,20-dien-24-oic acid δ lactone. M.p. 230° C.; $[\alpha]_D^{20}$=+80° (c=1, chloroform).

EXAMPLE 11

(17α,23R)-17-Hydroxy-11-methylene-3-oxo-19-norchola-4,20-diene-23-carboxylic acid δ lactone was prepared from (17α)-17-hydroxy-20-(hydroxymethyl)-11-methylene-19-norpregna-5,20-dien-3-one cyclic 1,2-ethanediyl acetal (Example 4, step ii) as follows:

i)—A solution of 7.72 g of the above diol in a mixture of 20 ml of dry THF, 20 ml of trimethyl orthopropionate and 0.18 ml of phosphorus oxychloride was stirred at room temperature for 1 h. The reaction mixture was then poured into 200 ml of water and the resulting suspension was stirred for 30 min. The product was taken up in ethyl acetate and the aqueous phase was extracted with the same solvent. The combined organic phases were washed with brine, dried over sodium sulfate, and concentrated under reduced pressure. Column chromatography gave 6.79 g of (17α)-20-(hydroxymethyl)-11-methylene-17-(1-oxopropoxy)-19-norpregna-5,20-dien-3-one cyclic 1,2-ethanediyl acetal.

ii)—Following a procedure analogous to that of step iv) of Example 4, 6.79 g of the steroid of the previous step was converted to 8.90 g of (17α)-11-methylene-20-[[[(4-methylphenyl)sulfonyl]oxy]methyl]-17-(1-oxopropoxy)-19-norpregna-5,20-dien-3-one cyclic 1,2-ethanediyl acetal, which were used in the following step without further purification.

iii)—A mixture of 300 ml of dry dimethoxyethane and 32 ml of a sodium bis(trimethylsilyl)amide solution (1N in THF) was cooled to −30° C. A solution of 4.77 g of the tosylate obtained in the previous step in 20 ml of dimethoxyethane was added dropwise and the mixture was stirred at −30° C. for 30 min. The reaction was quenched by addition of 100 ml of a saturated aqueous solution of ammonium chloride; the mixture was stirred at room temperature for 15 min and the dimethoxyethane and THF were removed under reduced pressure. The residue was extracted with ethyl acetate; the extracts were washed with brine, dried over sodium sulfate, and concentrated under reduced pressure to afford 3.48 g of (17α,23R)-3,3-[1,2-ethanediylbis(oxy)]-17-hydroxy-11-methylene-19-norchola-5,20-diene-23-carboxylic acid δ lactone, which were used in the following step without further purification.

iv)—Following a procedure analogous to that of step ii of Example 1, 1.36 g of the product of the previous step were converted to 0.84 g of (17α,23R)-17-hydroxy-11-methylene-3-oxo-19-norchola-4,20-diene-23-carboxylic acid δ lactone. M.p. 198° C.; $[\alpha]_D^{20}$=+98.5° (c=1, chloroform).

EXAMPLE 12

(17α)-17-Hydroxy-23-methyl-11-methylene-3-oxo-19-norchola-4,20-diene-23-carboxylic acid δ lactone was prepared from (17α)-11-methylene-20-[[[(4-methylphenyl)-sulfonyl]oxy]methyl]-17-(1-oxopropoxy)-19-norpregna-5,20-dien-3-one cyclic 1,2-ethanediyl acetal (Example 11, step ii) as follows:

i)—A mixture of 110 ml of dry dimethoxyethane and 12.8 ml of a sodium bis(trimethylsilyl)amide solution (1N in THF) was cooled to −30° C. A solution of 1.91 g of the tosylate mentioned above in 18 ml of dimethoxyethane was added dropwise and the mixture was stirred at −30° C. for 30 min. Iodomethane (1.99 ml) was added dropwise and the reaction mixture was allowed to warm to 0° C. in 2 h. A saturated aqueous solution of ammonium chloride was added and the dimethoxyethane and THF were removed under reduced pressure. The residue was extracted with ethyl acetate; the extracts were washed with brine, dried over sodium sulfate, and concentrated under reduced pressure to afford 1.43 g (100%) of (17α)-3,3-[1,2-ethanediylbis(oxy)]-17-hydroxy-23-methyl-11-methylene-19-norchola-5,20-diene-23-carboxylic acid δ lactone, which were used in the following step without further purification.

ii)—Following a procedure analogous to that described for step ii of Example 1, 1.43 g of the steroid mentioned above were converted to 0.95 g of (17α)-17-hydroxy-23-methyl-11-methylene-3-oxo-19-norchola-4,20-diene-23-carboxylic acid δ lactone. M.p. 235° C.; $[\alpha]_D^{20}$=+83.7° (c=1, chloroform).

EXAMPLE 13

(17α)-17-Hydroxy-11-methylene-3-oxo-19-norchola-4,20,22-triene-23-carboxylic acid δ lactone was prepared from (17α,23R)-3,3-[1,2-ethanediylbis(oxy)]-17-hydroxy-11-methylene-19-norchola-5,20-diene-23-carboxylic acid δ lactone (Example 11, step iii) as follows:

i)—A solution of 0.672 ml of diisopropylamine in 20 ml of dry THF was cooled to -30° C., and 3.00 ml of an n-butyllithium solution (1.6N in hexane) was added dropwise. The mixture was stirred for 10 min at -10° C. and then cooled to -78° C. A solution of 1.70 g of the steroid mentioned above in 20 ml of THF was added dropwise and stirring was continued for 15 min. A solution of 1.59 g of carbon tetrabromide in 8 ml of THF was added dropwise and the mixture was allowed to warm to 0° C. over 2 h. A saturated aqueous solution of ammonium chloride was added and the product was extracted into ethyl acetate. The combined organic phases were washed with brine, dried over sodium sulfate, and concentrated under reduced pressure to afford 1.93 g of (17α,23S)-23-bromo-3,3-[1,2-ethanediylbis(oxy)]-17-hydroxy-11-methylene-19-norchola-5,20-diene-23-carboxylic acid δ lactone, which were used in the next step without further purification.

ii)—A solution of 1.90 g of the bromosteroid obtained in the previous step in a mixture of 38 ml of toluene and 3.8 ml of 1,5-diazabicyclo[4.3.0]non-5-ene was stirred at room temperature for 1 h. The reaction mixture was poured into a saturated aqueous solution of sodium hydrogencarbonate and extracted with ethyl acetate. The combined organic phases were washed with brine, dried over sodium sulfate, and concentrated under reduced pressure to afford 1.38 g of (17α)-3,3-[1,2-ethanediylbis(oxy)]-17-hydroxy-11-methylene-19-norchola-5,20,22-triene-23-carboxylic acid δ lactone, which were used in the next step without further purification.

iii)—Following a procedure analogous to that of step ii of Example 1, 1.38 g of the steroid mentioned above were converted to 0.74 g of (17α)-17-hydroxy-11-methylene-3-oxo-19-norchola-4,20,22-triene-23-carboxylic acid δ lactone. M.p >230° C.; $[\alpha]_D^{20}$=+68.5° (c=1, chloroform).

EXAMPLE 14

(17α,22R)-22-Ethyl-17-hydroxy-11-methylene-3-oxo-19-norchola-4,20-dien-24-oic acid δ lactone was prepared from (17α)-3,3-[1,2-ethanediylbis(oxy)]-17-hydroxy-11-methylene-19-norpregna-5,20-diene-20-carboxaldehyde diethyl acetal (Example 4, step i) as follows:

i)—6.88 g of the steroid mentioned above were dissolved in 69 ml of dry THF. p-Toluenesulfonic acid (0.414 ml of a 1N aqueous solution) was added, and the mixture was stirred at room temperature for 45 min. The reaction mixture was then added dropwise to an ice-cooled mixture of 40 ml of a solution of ethylmagnesium bromide (3N in diethyl ether) and 100 ml of THF. The reaction mixture was stirred for 2 h, then it was quenched with a saturated aqueous solution of ammonium chloride. The product was extracted into ethyl acetate; the extracts were washed with brine, dried over sodium sulfate, and concentrated under reduced pressure. Column chromatography gave 3.31 g of (17α,22R)-17,22-dihydroxy-11-methylene-19-norchola-5,20-dien-3-one cyclic 1,2-ethanediyl acetal.

ii)—Following a procedure analogous to that of step iii of Example 4, 4.97 g of the steroid mentioned above were converted to 5.72 g of (17α,22R)-17-acetoxy-22-hydroxy-11-methylene-19-norchola-5,20-dien-3-one cyclic 1,2-ethanediyl acetal, which were used in the following step without further purification.

iii)—A solution of 2.28 g of the mono-ester obtained in the previous step in 16 ml of dry pyridine was cooled in a water bath. p-Toluenesulfonic anhydride (3.27 g) was added and the mixture was stirred at room temperature for 3 h. It was then poured into 320 ml of water and the resulting suspension was stirred for 1 h. The product was taken up into ethyl acetate and the aqueous layer was extracted with the same solvent. The combined organic phases were washed with a saturated aqueous solution of sodium hydrogencarbonate and with brine, dried over sodium sulfate, and concentrated under reduced pressure. The crude product (3.13 g) (17α,22R)-17-acetoxy-11-methylene-22-[[(4-methylphenyl)sulfonyl]-oxy]-19-norchola-5,20-dien-3-one cyclic 1,2-ethanediyl acetal, was used as such in the following step.

iv)—Following a procedure analogous to that of step v of Example 4, 3.13 g of the tosylate of the previous step were converted to 0.72 g of (17α,22R)-22-ethyl-3,3-[1,2-ethanediylbis(oxy)]-17-hydroxy-11-methylene-19-norchola-5,20-dien-24-oic acid δ lactone.

v)—Following a procedure analogous to that of step ii of Example 1, 0.72 g of the steroid from the previous step were converted to 0.44 g of (17α,22R)-22-ethyl-17-hydroxy-11-methylene-3-oxo-19-norchola-4,20-dien-24-oic acid δ lactone. M.p. 172° C.; $[\alpha]_D^{20}$=+186° (c=1, chloroform).

EXAMPLE 15

(3β,17α)-3,17-Dihydroxy-11-methylene-19-norchola-4,20-dien-24-oic acid δ lactone was prepared from (17α)-17-hydroxy-11-methylene-3-oxo-19-norchola-4,20-dien-24-oic acid δ lactone (from Example 2) as follows:

Sodium borohydride (0.522 g) was added to a solution of 2.52 g of the latter steroid in 69 ml of dry diglyme. The reaction mixture was stirred at room temperature for 1 h. After cooling to 0° C., the reaction was quenched with an aqueous solution of acetic acid (10%). The resulting mixture was poured into 240 ml of water and the product was extracted into diethyl ether. The combined organic phases were washed with water, with a saturated aqueous solution of sodium hydrogencarbonate, and with brine, dried over sodium sulfate, and concentrated under reduced pressure to give an epimeric mixture of reduction products. The 3β-hydroxy isomer was isolated by column chromatography, affording 0.40 g of (3β,17α)-3,17-dihydroxy-11-methylene-19-norchola-4,20-dien-24-oic acid δ lactone. M.p. 211° C.; $[\alpha]_D^{20}$=+19.8° (c=1, chloroform).

EXAMPLE 16

(3β,17α)-17-Hydroxy-3-methoxy-11-methylene-19-norchola-4,20-dien-24-oic acid δ lactone (a) and (3α,17α)-

17-hydroxy-3-methoxy-11-methylene-19-norchola-4,20-dien-24-oic acid δ lactone (b) were prepared from (17α)-17-hydroxy-20-(hydroxymethyl)-11-methylene-19-norpregna-5,20-dien-3-one cyclic 1,2-ethanediyl acetal (Example 4, step ii) as follows:

i)—A solution of 4.59 g of the latter steroid in a mixture of 90 ml of methanol and 4.6 ml of 6N hydrochloric acid was stirred at room temperature for 2 h. Water (90 ml) was added; the resulting suspension was filtered and the residue was washed with water. Drying of the residue afforded 3.86 g of (17α)-17-hydroxy-20-(hydroxymethyl)-11-methylene-19-norpregna-4,20-dien-3-one, which were used as such in the following step.

ii)—A solution of 3.17 g of the product obtained in the previous step and 0.176 g of p-toluenesulfonic acid in 93 ml of acetone was stirred at room temperature for 48 h. The reaction mixture was neutralized by addition of a saturated aqueous solution of sodium hydrogencarbonate, and the acetone was removed under reduced pressure. The residue was extracted with ethyl acetate; the extracts were washed with brine, dried over sodium sulfate, and concentrated under reduced pressure to give 2.51 g of (17'β)-2,2-dimethyl-5,11'-dimethylenespiro-[1,3-dioxane-4,17'-estr[4]ene]-3'-one, which were used as such in the following step.

iii)—A solution of 2.51 g of the steroid obtained in the previous step in 50 ml of dry THF was added dropwise to an ice-cooled suspension of 1.25 g of lithium aluminium hydride in 50 ml of THF. After 1 h at 0° C., the reaction was quenched with a saturated aqueous solution of sodium sulfate. Ethyl acetate was added, and the mixture was filtered over celite. The filtrate was concentrated under reduced pressure to give 2.53 g of a 85:15 mixture of (3'β,17'β)-2,2-dimethyl-5,11'-dimethylenespiro[1,3-dioxane-4,17'-estr[4]ene]-3'-ol and (3'α, 17'β)-2,2-dimethyl-5,11'-dimethylenespiro[1,3-dioxane-4,17'-estr[4]ene]-3'-ol, which were used as such in the following step.

iv)—A solution of 2.53 g of the product of the previous step in a mixture of 26.4 ml of pyridine and 13.2 ml of acetic anhydride was stirred at room temperature for 6 h. The reaction mixture was then poured into 300 ml of water and the resulting suspension was stirred for 30 min. The product was taken up into ethyl acetate and the aqueous layer was extracted with the same solvent. The combined organic phases were washed with a saturated aqueous solution of sodium hydrogencarbonate and with brine, dried over sodium sulfate, and concentrated under reduced pressure to give 2.73 g of a 85:15 mixture of (3'β,17'β)-2,2-dimethyl-5,11'-dimethylenespiro[1,3-dioxane-4,17'-estr[4]ene]-3'-ol acetate and (3'α,17'β)-2,2-dimethyl-5,11'-dimethylenespiro[1,3-dioxane-4,17'-estr-[4]ene]-3'-ol acetate, which were used as such in the following step.

v)—Following a procedure analogous to that of step i, 2.73 g of the product of the previous step were converted to 2.22 g of a 6:4 mixture of (3β,17α)-3-methoxy-11,20-dimethylene-19-norpregn-4-ene-17,21-diol and (3α,17α)-3-methoxy-11,20-dimethylene-19-norpregn-4-ene-17,21-diol, which were used as such in the following step.

vi)—Following a procedure analogous to that of step iii of Example 4, 2.22 g of the product of the previous step were acetylated at the 17-hydroxy group giving 1.04 g of (3β,17α)-3-methoxy-11,20-dimethylene-19-norpregn-4-ene-17,21-diol 17-acetate and 0.75 g of (3α,17α)-3-methoxy-11,20-dimethylene-19-norpregn-4-ene-17,21-diol 17-acetate.

viia)—Following a procedure analogous to that of step iv of Example 4, 1.04 g of (3β,17α)-3-methoxy-11,20-dimethylene-19-norpregn-4-ene-17,21-diol 17-acetate were converted to 1.24 g of (3β,17α)-3-methoxy-11,20-dimethylene-19-norpregna-4,20-diene-17,21-diol 17-acetate 21-(4-methylbenzenesulfonate), which were used as such in the following step.

viiia)—Following a procedure analogous to that described for step v of Example 4, 1.24 g of the product of the previous step were converted to 0.66 g of (3β,17α)-17-hydroxy-3-methoxy-11-methylene-19-norchola-4,20-dien-24-oic acid δ lactone. M.p. 121° C.; $[α]_D^{20}=+15.3°$ (c=1, chloroform).

viib)—Following a procedure analogous to that of step iv of Example 4, 0.75 g of (3α,17α)-3-methoxy-11,20-dimethylene-19-norpregn-4-ene-17,21-diol 17-acetate were converted to 0.97 g of (3α,17α)-3-methoxy-11,20-dimethylene-19-norpregna-4,20-diene-17,21-diol 17-acetate 21-(4-methylbenzenesulfonate), which were used as such in the following step.

viiib)—Following a procedure analogous to that of step v of Example 4, 0.97 g of the product of the previous step were converted to 0.53 g of (3α,17α)-17-hydroxy-3-methoxy-11-methylene-19-norchola-4,20-dien-24-oic acid δ lactone. M.p. 150° C.; $[α]_D^{20}=+76°$ (c=1, chloroform).

EXAMPLE 17

(11β,17α)-11-Ethyl-17-hydroxy-3-oxo-19-norchola-4,9,20-trien-24-oic acid δ lactone was prepared from estra-5(10),9(11)-diene-3,17-dione cyclic 3-(1,2-ethanediyl acetal) as follows:

i)—Following a procedure analogous to that of step i of Example 1, 29.7 g of the latter steroid were converted to 42.07 g of a mixture of starting material and (17α)-17-hydroxy-24-trimethylsilyloxy-19-norchola-5(10),9(11),20-trien-3-one cyclic 1,2-ethanediyl acetal, which were used as such in the following step.

ii)—A mixture of 110 g of silica, 9.8 ml of a saturated aqueous solution of oxalic acid and 310 ml of dichloromethane was stirred for 10 min. A solution of 42.07 g of the product of the previous step in 130 ml of dichloromethane was added and stirring was continued for another 20 min. Sodium hydrogencarbonate (5 g) was added and the mixture was filtered over celite. The residue was washed with ethyl acetate and the filtrate was concentrated under reduced pressure to give 8.22 g of (17α)-17,24-dihydroxy-19-norchola-5(10),9(11),20-trien-3-one cyclic 1,2-ethanediyl acetal.

iii)—To a solution of 8.22 g of the product of the previous step in 113 ml of dichloromethane were added 0.51 ml of pyridine, 1.92 ml of 2,2,2-trifluoroacetophenone and 27.7 ml of an aqueous solution of hydrogen peroxide (30%). After stirring at room temperature for 70 h, the reaction mixture was poured into 300 ml of water. The aqueous layer was extracted with dichloromethane; the combined organic phases were washed repeatedly with a saturated aqueous solution of sodium thiosulfate and with brine, dried over sodium sulfate, and concentrated under reduced pressure. Column chromatography gave 3.26 g of (5α,10α,17α)-5,10-epoxy-17,24-dihydroxy-19-norchola-9(11),20-dien-3-one cyclic 1,2-ethanediyl acetal.

iv)—To a mixture of 3.26 g of the steroid mentioned above and 0.47 g of copper(I) bromide-dimethyl sulfide complex in 78 ml of dry THF, cooled to −20° C., were added dropwise 16 ml of an ethylmagnesium bromide solution (3N in diethyl ether). After stirring at −20° C. for 1 h, the reaction was quenched with a saturated aqueous solution of ammonium chloride. The product was extracted into ethyl acetate; the extracts were washed with brine, dried over sodium sulfate, and concentrated under reduced pressure to give 3.05 g of (5α,11β,17α)-11-ethyl-5,17,24-trihydroxy-19-norchola-9,20-dien-3-one cyclic 1,2-ethanediyl acetal, which were used as such in the following step.

v)—Following a procedure analogous to that of step ii of Example 1, 3.05 g of the steroid of the previous step were converted to 1.38 g of (11β,17α)-11-ethyl-17,24-dihydroxy-19-norchola-4,9, 20-trien-3-one.

vi)—To a solution of 23.1 g of pyridinium dichromate in 84 ml of dry dimethyl formamide was added a solution of 1.38 g of the product of the previous step in 35 ml of the same solvent. The reaction mixture was stirred at room temperature for 45 min and then poured into 1200 ml of water. The product was extracted into ethyl acetate; the combined extracts were washed with water (3 times) and with brine, dried over sodium sulfate, and concentrated under reduced pressure. Column chromatography gave 0.78 g of (11β,17α)-11-ethyl-17-hydroxy-3-oxo-19-norchola-4, 9,20-trien-24-oic acid δ lactone. M.p. 207° C.; $[\alpha]_D^{20}$=−185° (c=1, chloroform).

EXAMPLE 18

(17α)-17-Hydroxy-3-oxo-19-norchola-4,20,22-trien-24-oic acid δ lactone was prepared from (17α)-3,3-[1,2-ethanediylbis(oxy)]-17-hydroxy-19-norpregna-5,20-diene-20-carboxaldehyde diethyl acetal, in its turn prepared from estr-5-ene-3,17-dione cyclic 3-(1,2-ethanediyl acetal) by a procedure analogous to that of step i of Example 4, as follows:

i)—16.30 g of (17α)-3,3-[1,2-ethanediylbis(oxy)]-17-hydroxy-19-norpregna-5,20-diene-20-carboxaldehyde diethyl acetal was dissolved in 180 ml of dry THF. p-Toluenesulfonic acid (1.10 ml of a 1N aqueous solution) was added, and the mixture was stirred at room temperature for 4 h. A saturated aqueous solution of sodium hydrogencarbonate was added and the product was extracted into ethyl acetate. The combined organic phases were washed with brine, dried over sodium sulfate, and concentrated under reduced pressure to give 12.53 g of (17α)-3,3-[1,2-ethanediylbis(oxy)]-17-hydroxy-19-norpregna-5,20-diene-20-carboxaldehyde, which were used as such in the following step.

ii)—Chlorotrimethylsilane (3.4 ml) was added to an ice-cooled solution of 2.0 g of the product of the previous step in a mixture of 30 ml of dichloromethane and 4.4 ml of pyridine. The reaction mixture was stirred at room temperature for 20 h and then poured into a saturated aqueous solution of sodium hydrogencarbonate. The product was extracted into dichloromethane; the extracts were washed with brine, dried over sodium sulfate, and concentrated under reduced pressure to give 2.59 g of (17α)-3,3-[1,2-ethanediylbis(oxy)]-17-trimethylsilyloxy-19-norpregna-5, 20-diene-20-carboxaldehyde which were used as such in the following step.

iii)—A solution of 1.32 ml of diisopropylamine in 45 ml of dry THF was cooled to −30° C., and 6.10 ml of an n-butyllithium solution (1.6N in hexane) were added dropwise. The mixture was stirred for 10 min at −10° C. and then cooled to −78° C. t-Butyl acetate (1.28 ml) was added dropwise and stirring was continued for 30 min. A solution of 2.07 g of the product of the previous step in 8 ml of THF was added dropwise and the reaction mixture was stirred for another 2.5 h. A saturated aqueous solution of ammonium chloride was added and the product was extracted into ethyl acetate. The combined organic phases were washed with brine, dried over sodium sulfate, and concentrated under reduced pressure. Column chromatography gave 0.52 g of 1,1-dimethylethyl (17α,22S)-3,3-[1,2-ethanediylbis(oxy)]-22-hydroxy-17-trimethylsilyloxy-19-norchola-5,20-dien-24-oate, and 2.02 g of 1,1-dimethylethyl (17α,22R)-3,3-[1, 2-ethanediylbis(oxy)]-22-hydroxy-17-trimethylsilyloxy-19-norchola-5,20-dien-24-oate.

iv)—Powdered potassium hydroxide (0.546 g) was added to a solution of 2.02 g of the major product of the previous step in 1.4 ml of dry methanol and 12.3 ml of dry THF. After stirring for 3 h at room temperature, the reaction mixture was neutralized with an aqueous solution of acetic acid (50%), poured into 150 ml of water and extracted with dichloromethane. The combined organic phases were washed with brine, dried over sodium sulfate, and concentrated under reduced pressure. Column chromatography gave 0.503 g of (17α)-3,3-[1,2-ethanediylbis(oxy)]-17-hydroxy-19-norchola-5,20,22-trien-24-oic acid δ lactone and 0.255 g of (17α,22R)-3,3-[1,2-ethanediylbis(oxy)]-17, 22-dihydroxy-19-norchola-5,20-dien-24-oic acid δ lactone.

v)—Following a procedure analogous to that of step ii of Example 1, 0.453 g of the major product of the previous step was converted to 0.402 g of (17α)-17-hydroxy-3-oxo-19-norchola-4,20,22-trien-24-oic acid δ lactone. M.p. >250° C.; $[\alpha]_D^{20}$=−29.6° (c=0.5, chloroform).

EXAMPLE 19

Following a procedure analogous to that of step ii of Example 1, (17α,22R)-17,22-dihydroxy-3-oxo-19-norchola-4,20-dien-24-oic acid δ lactone was prepared from (17α,22R)-3,3-[1,2-ethanediylbis(oxy)]-17,22-dihydroxy-19-norchola-5,20-dien-24-oic acid δ lactone (Example 18, step iv). M.p. 235° C.

EXAMPLE 20

(17α,22S)-17,22-Dihydroxy-3-oxo-19-norchola-4,20-dien-24-oic acid δ lactone was prepared from 1,1-dimethylethyl (17α,22S)-3,3-[1,2-ethanediylbis(oxy)]-22-hydroxy-17-trimethylsilyloxy-19-norchola-5,20-dien-24-oate (Example 18, step iii) as follows:

i)—Powdered potassium hydroxide (0.580 g) was added to a solution of 2.15 g of the latter steroid in 1.5 ml of dry methanol and 13 ml of dry THF. After stirring for 75 min at room temperature, the reaction mixture was poured into 150 ml of water and extracted with ethyl acetate. The organic phases were discarded; the aqueous phase was acidified (to pH 3) with an aqueous solution of acetic acid (50%) and then extracted with dichloromethane. The combined dichloromethane extracts were dried over sodium sulfate and concentrated under reduced pressure to give 1.20 g of (17α,22S)-3,3-[1,2-ethanediylbis(oxy)]-17,22-dihydroxy-19-norchola-5,20-dien-24-oic acid, which were used as such in the following step.

ii)—Following a procedure analogous to that of step ii of Example 1, using THF as the solvent, 1.20 g of the product of the previous step were converted to 0.455 g of (17α,22S)-17,22-dihydroxy-3-oxo-19-norchola-4,20-dien-24-oic acid δ lactone. M.p. 229° C.; $[\alpha]_D^{20}$=+58.4° (c=0.5, chloroform).

EXAMPLE 21

(17α)-23-Bromo-17-hydroxy-3-oxo-19-norchola-4,20, 22-trien-24-oic acid δ lactone was prepared from (17α)-3, 3-[1,2-ethanediylbis(oxy)]-17-hydroxy-19-norchola-5,20-dien-24-oic acid δ lactone, which was prepared using a procedure analogous to that described in Example 4, as follows:

i)—Following a procedure analogous to that of step i of Example 13, 10.05 g of the lactone mentioned above were converted to 4.17 g of (17α)-23,23-dibromo-3,3-[1,2-ethanediylbis(oxy)]-17-hydroxy-19-norchola-5,20-dien-24-oic acid δ lactone.

ii)—Following a procedure analogous to that of step ii of Example 13, 4.17 g of the steroid of the previous step were converted to 1.30 g of (17α)-23-bromo-3,3-[1,2-ethanediylbis(oxy)]-17-hydroxy-19-norchola-5,20,22-trien-24-oic acid δ lactone.

iii)—Following a procedure analogous to that of step ii of Example 1, 1.38 g of the product of the previous step were converted to 1.17 g of (17α)-23-bromo-17-hydroxy-3-oxo-19-norchola-4,20,22-trien-24-oic acid δ lactone. M.p. 209° C.; $[α]_D^{20}$=−71.4° (c=0.5, chloroform).

EXAMPLE 22

(17α)-17-Hydroxy-3-oxo-19-norchola-4,6,20-trien-24-oic acid δ lactone was prepared from (17α)-3-ethoxy-24-trimethylsilyloxy-19-norchola-3,5,20-trien-17-ol (Example 1, step i) as follows:

i)—A solution of 11.4 g of the steroid mentioned above in 20 ml of dichloromethane was added under vigorous stirring to mixture of 8.2 g of tetrachloro-1,4-benzoquinone, 18 ml of methanol, 43 ml of dichloromethane, 1.0 ml of water, 1.7 ml of acetic acid, and 0.18 ml of pyridine. After 75 min stirring, a solution of 3.25 g of sodium hydroxide and 3.25 g of sodium hydrosulfite in 50 ml of water was added and stirring was continued for 30 min. The product was extracted into dichloromethane; the combined organic phases were washed with an aqueous solution of sodium hydroxide (2N), water, and with brine, dried over sodium sulfate, and concentrated under reduced pressure. Column chromatography afforded 2.39 g of (17α)-17,24-dihydroxy-19-norchola-4,6,20-trien-3-one.

ii)—Following a procedure analogous to that of step vi of Example 17, 2.39 g of the steroid of the previous step were converted to 1.70 g of (17α)-17-hydroxy-3-oxo-19-norchola-4,6,20-trien-24-oic acid δ lactone. M.p. 230° C.; $[α]_D^{20}$=−94.8° (c=1, chloroform).

EXAMPLE 23

(7α,17α)-17-Hydroxy-7-methyl-3-oxo-19-norchola-5(10),20-dien-24-oic acid δ lactone was prepared from (7α)-7-methylestr-5(10)-ene-3,17-dione 3-(dimethyl acetal) as follows:

i)—Following a procedure analogous to that of step i of Example 1, 30.0 g of the latter steroid were converted to 45.1 g of a mixture of starting material and (7α,17α)-17-hydroxy-7-methyl-24-trimethylsilyloxy-19-norchola-5(10),20-dien-3-one dimethyl acetal, which were used as such in the following step.

ii)—256 ml of a solution of tetrabutylammonium fluoride (1N in THF) were added to an ice-cooled solution of 45.1 g of the steroid of the previous step in 128 ml of dry THF. The reaction mixture was stirred at 0° C. for 45 min and then poured into 2 l of water. The product was extracted into ethyl acetate; the combined organic phases were washed with water, a saturated aqueous solution of sodium hydrogencarbonate, and brine, dried over sodium sulfate, and concentrated under reduced pressure. Column chromatography afforded 15.55 g of (7α,17α)-17,24-dihydroxy-7-methyl-19-norchola-5(10),20-dien-3-one dimethyl acetal.

iii)—A mixture of 200 ml of dichloromethane and 40 ml of pyridine was cooled in a water bath. Chromium(VI) oxide (24.8 g) was added carefully, and the mixture was stirred for 10 min. A solution of 7.0 g of the product of the previous step in a mixture of 1 ml of pyridine and 250 ml of dichloromethane was added and the reaction mixture was stirred at room temperature for 1 h. It was then poured into an aqueous solution of sodium hydrogen-sulfite (10%) and extracted with ethyl acetate. The combined organic phases were washed with a saturated aqueous solution of sodium hydrogencarbonate and with brine, dried over sodium sulfate, and concentrated under reduced pressure. Column chromatography afforded 5.47 g of (7α,17α)-17-hydroxy-3,3-dimethoxy-7-methyl-19-norchola-5(10),20-dien-24-oic acid δ lactone.

iv)—A solution of 0.070 g of oxalic acid dihydrate in 7.0 ml of water was added to a solution of 1.36 g of the product of the previous step in 27 ml of ethanol. The reaction mixture was stirred at 30° C. for 30 min. Triethylamine (1 ml) was added and the mixture was poured into a saturated aqueous solution of sodium hydrogencarbonate. The product was extracted into ethyl acetate; the combined organic phases were washed with brine, dried over sodium sulfate, and concentrated under reduced pressure. Column chromatography afforded 1.03 g of (7α,17α)-17-hydroxy-7-methyl-3-oxo-19-norchola-5(10), 20-dien-24-oic acid δ lactone. M.p. 77° C.; $[α]_D^{20}$=+53° (c=1, chloroform).

EXAMPLE 24

(11β,17α)-17-Hydroxy-3-(hydroxyimino)-11-(1-propynyl)-19-norchola-4,20-dien-24-oic acid δ lactone was prepared from (11β,17α)-17-hydroxy-3-oxo-11-(1-propynyl)-19-norchola-4,20-dien-24-oic acid δ lactone (see Example 2) as follows:

To a solution of 1.95 g of the above lactone in 8.5 ml of pyridine were added 3.80 g of hydroxylamine hydrochloride. The reaction mixture was stirred at room temperature for 1 h and then poured into 150 ml of water. The product was extracted into dichloromethane; the combined organic phases were washed with water, dried over sodium sulfate, and concentrated under reduced pressure. Column chromatography gave 1.94 g of (11β,17α)-17-hydroxy-3-(hydroxyimino)-11-(1-propynyl)-19-norchola-4,20-dien-24-oic acid δ lactone as a 45:55 mixture of E/Z epimers. M.p >250° C.; $[α]_D^{20}$=+173.6° (c=0.5, chloroform).

EXAMPLE 25

(3E,11β,17α)-3-(Acetoxyimino)-17-hydroxy-11-methyl-19-norchola-4,20-dien-24-oic acid δ lactone (a) and (3Z,11β,17α)-3-(acetoxyimino)-17-hydroxy-11-methyl-19-norchola-4,20-dien-24-oic acid δ lactone (b) were prepared from (11β,17α)-17-hydroxy-11-methyl-3-oxo-19-norchola-4,20-dien-24-oic acid δ lactone (see Example 2) as follows:

To a solution of 2.4 g of the above lactone in 12 ml of pyridine were added 5.04 g of hydroxylamine hydrochloride. The reaction mixture was then stirred at 80° C. for 4 h. After cooling, the mixture was poured into 150 ml of ice-water and stirred for 30 min. The resulting suspension was filtered; the residue washed thoroughly with water and dried under reduced pressure at 50° C. The product was taken up in a mixture of 24 ml of pyridine and 12 ml of acetic anhydride. The reaction mixture was stirred at room temperature for 2 h and subsequently poured into 800 ml of ice-water. The resulting precipitate was collected and dried under reduced pressure. Column chromatography of the solid thus obtained afforded 0.85 g of (3E,11β,17α)-3-(acetoxyimino)-17-hydroxy-11-methyl-19-norchola-4,20-dien-24-oic acid δ lactone, M.p. 194° C.; $[α]_D^{20}$=+63.6° (c=1, chloroform), and 0.29 g of (3Z,11β,17α)-3-(acetoxyimino)-17-hydroxy-11-methyl-19-norchola-4,20-dien-24-oic acid δ lactone, M.p. 182° C.; $[α]_D^{20}$=+122.3° (c=1, chloroform).

EXAMPLE 26

(17α,23Z)-17,24-Dihydroxy-11-methylene-3-oxo-19-norchola-4,20,23-triene-23-carboxylic acid δ lactone was prepared from (17α)-3,3-[1,2-ethanediylbis(oxy)]-17-hydroxy-11-methylene-19-norchola-5,20-dien-24-oic acid δ lactone (Example 4, step v) as follows:

i)—A solution of 1.68 ml of diisopropylamine in 24 ml of dry THF was cooled to −30° C., and 7.5 ml of an n-butyllithium solution (1.6N in hexane) were added dropwise. The mixture was stirred for 10 min at −10° C. and then cooled to −78° C. A solution of 1.64 g of the steroid mentioned above in 20 ml of THF was added dropwise and stirring was continued for 15 min. Ethyl formate (2.24 ml) was added and the mixture was allowed to warm to 0° C. over 2 h. A saturated aqueous solution of ammonium chloride was added and the product was extracted into ethyl acetate. The combined organic phases were washed with brine, dried over sodium sulfate, and concentrated under reduced pressure affording 2.09 g of (17α,23Z)-3,3-[1,2-ethanediylbis(oxy)]-17,24-dihydroxy-11-methylene-19-norchola-5,20,23-triene-23-carboxylic acid δ lactone, which were used in the following step without further purification.

ii)—Following a procedure analogous to that of step ii of Example 1, 2.09 g of the product of the previous step were converted to 0.39 g of (17α,23Z)-17,24-dihydroxy-11-methylene-3-oxo-19-norchola-4,20,23-triene-23-carboxylic acid δ lactone. M.p. >105° C., dec.

EXAMPLE 27

(17α,23Xi)-17-Hydroxy-11-methylene-3,24-dioxo-19,26,27-trinorcholesta-4,20-diene-23-carboxylic acid δ lactone was prepared from (17α)-3,3-[1,2-ethanediylbis(oxy)]-17-hydroxy-11-methylene-19-norchola-5,20-dien-24-oic acid δ lactone (Example 4, step v) as follows:

i)—A solution of 1.26 ml of diisopropylamine in 18 ml of dry THF was cooled to −30° C., and 5.63 ml of an n-butyllithium solution (1.6N in hexane) were added dropwise. The mixture was stirred for 10 min at −10° C. and then cooled to −78° C. A solution of 1.23 g of the steroid mentioned above in 16 ml of THF was added dropwise and stirring was continued for 15 min. Acetyl chloride (0.852 ml) was added and the mixture was allowed to warm to 0° C. over 2 h. A saturated aqueous solution of ammonium chloride was added and the product was extracted into ethyl acetate. The combined organic phases were washed with brine, dried over sodium sulfate, and concentrated under reduced pressure affording 2.10 g of (17α,23Xi)-3,3-[1,2-ethanediylbis(oxy)]-17-hydroxy-11-methylene-24-oxo-19,26,27-trinorcholesta-5,20-diene-23-carboxylic acid δ lactone, which were used in the following step without further purification.

ii)—Following a procedure analogous to that of step ii of Example 1, 2.10 g of the product of the previous step were converted to 0.33 g of (17α,23Xi)-17-hydroxy-11-methylene-3,24-dioxo-19,26,27-trinorcholesta-4,20-diene-23-carboxylic acid δ lactone. M.p. 190° C.

EXAMPLE 28

(11β,17α)-17-Hydroxy-11-methyl-3-oxo-19-norchola-4,20-diene-24-carboxylic acid ε lactone was prepared from (11β)-11-methylestr-5-ene-3,17-dione cyclic 3-(1,2-ethanediyl acetal) and 2-bromo-6-trimethylsilyloxy-1-hexene as outlined in Example 1. M.p. 230.1° C.

EXAMPLE 29

Receptor binding affinities of the compounds of the invention.

The progesterone affinity of the compounds of the invention was measured for cytoplasmic progesterone receptors present in human breast tumor cells (MCF-7 cells, incubation time 16 h, temperature 4° C.) and compared with the affinity of (16α)-16-ethyl-21-hydroxy-19-norpregn-4-ene-3,20-dione (according to the procedure described by E. W. Bergink et al., J. Steroid Biochem., Vol. 19, 1563–1570 (1983)).

The glucocorticoid affinity of the compounds of the invention was measured for glucocorticoid receptors present in intact human multiple myeloma cells (IM-9 cells, incubation time 1 h, temperature 37° C.) and compared with the affinity of dexamethasone (according to the procedure described by H. J. Kloosterboer et al., J. Steroid Biochem., Vol. 31, 567–571 (1988)).

In Table I the receptor binding affinities of compounds of the invention to the progesterone receptor (PR), to the glucocorticoid receptor (GR), and their ratio (PR/GR) are given.

TABLE I

| Product of example: | PR | GR | PR/GR |
|---|---|---|---|
| 1 | 235 | 14 | 16.8 |
| 2(a) | 246 | 108 | 2.3 |
| 2(b) | 270 | 67 | 4.0 |
| 2(c) | 316 | 104 | 3.0 |
| 2(d) | 62 | 7 | 8.9 |
| 2(f) | 290 | 230 | 1.3 |
| 2(g) | 283 | 82 | 3.5 |
| 2(h) | 293 | 89 | 3.3 |
| 2(i) | 215 | 36 | 6.0 |
| 2(j) | 213 | 56 | 3.8 |
| 2(k) | 33 | 25 | 1.3 |
| 2(l) | 265 | 26 | 10.2 |
| 2(m) | 242 | 42 | 5.8 |
| 2(n) | 200 | 28 | 7.1 |
| 2(o) | 220 | 96 | 2.3 |
| 3 | 184 | 49 | 3.8 |
| 5(b) | 31 | 1 | 31.0 |
| 5(c) | 129 | 5 | 25.8 |
| 6 | 400 | 80 | 5.0 |
| 7 | 35 | 2 | 17.5 |
| 8 | 178 | 131 | 1.4 |
| 9 | 132 | 84 | 1.6 |
| 10 | 93 | 41 | 2.3 |
| 11 | 365 | 97 | 3.8 |
| 12 | 47 | 10 | 4.7 |
| 13 | 345 | 71 | 4.9 |
| 14 | 171 | 9 | 19.0 |
| 15 | 94 | 10 | 9.4 |
| 16(a) | 3 | 4 | 0.8 |
| 16(b) | 1 | 0.3 | 3.3 |
| 17 | 71 | 28 | 2.5 |
| 18 | 146 | 4 | 36.5 |
| 19 | 26 | 1 | 26.0 |
| 20 | 4 | <1 | >4 |
| 21 | 16 | 4 | 4.0 |
| 22 | 111 | 2 | 55.5 |
| 23 | 11 | 1 | 11.0 |
| 24 | 225 | 113 | 2.0 |
| 25(a) | 203 | 200 | 1.0 |
| 25(b) | 170 | 18 | 9.4 |
| 26 | 8 | 2 | 4.0 |
| 27 | 17 | 5 | 3.4 |
| 28 | 32 | 7 | 4.6 |

The compounds of the present invention were compared with the prior art compounds of EP-A-558,416 (page 15):

TABLE II

Receptor binding affinities of the compounds of EP-A-558,416

| Product of example: | PR* | GR* | PR/GR |
|---|---|---|---|
| 1 | 21 | 94 | 0.22 |
| 2 | 36 | 59 | 0.61 |

*PR and GR data from EP-A-558,416, p. 15. Incubation time 24 h at 0° C.;

Conclusion: The compounds of the invention have a much higher PR/GR ratio than the prior art compounds, which ratio's are usually >1 in contrast to the prior art compounds, which PR/GR ratio's are <1. This means that the prior art compounds show relatively higher receptor binding affinity to the glucocorticoid receptor than to the progesterone receptor, whereas the compounds of the invention have a relatively favourable affinity to the progesterone receptor and relatively low affinity to the unfavourable glucocorticoid receptor. Compounds having relatively low affinity to the progesterone receptor may be suitable pro-drugs.

We claim:

1. A steroid with a 17-spiro[methylene lactone] or 17-spiro[methylene lactol] group having formula I

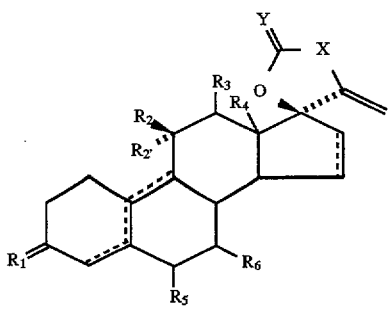

wherein $R_1$ is O, (H,H), (H,OR), or NOR, R being selected from H, (1–6C) alkyl and (1–6C) acyl;

$R_2$ is H, (1–6C) alkyl optionally substituted by a halogen, (2–6C) alkenyl optionally substituted by a halogen, (2–6C) alkynyl optionally substituted by a halogen, or halogen;

$R_2'$ is H; or $R_2'$ together with $R_2$ is a (1–6C) alkylidene group or a (2–6C) alkenylidene group; or $R_2'$ together with $R_3$ is a bond;

$R_3$ is H if not together with $R_2'$ a bond;

$R_4$ is (1–6C) alkyl; one of $R_5$ and $R_6$ is hydrogen and the other is hydrogen or (1–6C) alkyl;

X is $(CH_2)_n$ or $(C_nH_{2n-2})$ wherein n is 2 or 3, wherein $(CH_2)_n$ is optionally substituted with hydroxy, halogen, (1–6C) alkyl, (1–6C) aliphatic hydrocarbon acyl, (7–9C) phenylalkyl, the phenyl group of which may be substituted with (1–6C) alkyl, (1–6C) alkoxy, hydroxy or halogen;

Y is O or (H,OH); and the dotted lines indicate optional bonds, at least one of bonds 4–5, 5–10, and 9–10 being a double bond.

2. The steroid of claim 1 wherein $R_1$ is O; $R_4$ is methyl, Y is O, and n is 2.

3. The steroid of claim 2 wherein $R_1$ is O, $R_2$ is (1–6C) alkyl or (2–6C) alkynyl, $R_2'$ and $R_3$ are H, $R_4$ is methyl, $R_5$ and $R_6$ are hydrogen, X is $(CH_2)_2$, Y is O, and the dotted line in the D-ring is not a bond and the other dotted line is a 4–5 bond.

4. The steroid of claim 1 having the formula (11β,17α)-11-ethyl-17-hydroxy-3-oxo-19-norchola-4,20-dien-24-oic acid δ-lactone or (11β,17α)-17-hydroxy-3-oxo-11-(1-propynyl)-19-norchola-4,20-dien-24-oic acid δ-lactone.

5. A method of preparation of a steroid of claim 1 having formula I, wherein a compound having the formula III

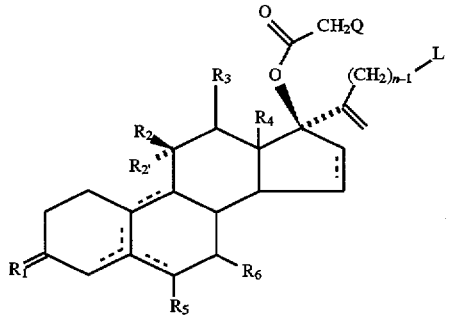

wherein $R_1'$ is O, (H,H) or (H,OR), R being selected from H, (1–6C) alkyl and (1–6C) aliphatic hydrocarbon acyl, or a protected derivative thereof;

$R_2$ is H, (1–6C) alkyl optionally substituted by a halogen, (2–6C) alkenyl optionally substituted by a halogen, (2–6C) alkynyl optionally substituted by a halogen, or halogen;

$R_2'$ is H; or $R_2'$ together with $R_2$ is a (1–6C) alkylidene group or a (2–6C) alkenylidene group; or $R_2'$ together with $R_3$ is a bond;

$R_3$ is H if not together with $R_2'$ a bond;

$R_4$ is (1–6C) alkyl; one of $R_5$ and $R_6$ is hydrogen and the other is hydrogen or (1–6C) alkyl;

each Q is independently selected from H, (1–6C) alkyl and (7–9C) phenylalkyl, the phenyl group of which may be substituted with (1–6C) alkyl, (1–6C) alkoxy, hydroxy or halogen;

n is 2 or 3;

L is a leaving group; and the dotted lines indicate optional bonds, at least one of bonds 4–5, 5–6, 5–10, and 9–10 being a double bond, is converted by base-catalyzed ring-closure into a steroid with a 17-spiromethylene lactone group, wherein the ring-closure is optionally followed by: alkylation, phenylalkylation, acylation, halogenation, or halogenation and subsequent dehydrohalogenation, at the carbon atom adjacent to the lactone carbonyl; a reduction reaction to produce a steroid of claim 1 wherein Y is (H,OH), after which the optionally present protective group is removed; and reacting with hydroxylamine to prepare the steroid of claim 1 wherein $R_1$ is NOR, R being hydrogen.

6. A pharmaceutical composition comprising the steroid of claim 1 and pharmaceutically acceptable auxiliaries.

7. A method of contraception, comprising administering an effective amount of the steroid of claim 1 to a mammal.

8. A method of contraception, comprising administering an effective amount the steroid of claim 1 to an animal.

9. A method for treating menstrual disorders, comprising administering an effective amount of the steroid of claim 1.

10. A method for treating female hormone-responsive tumors, comprising administering an effective amount of the steroid of claim 1.

11. A method for hormone replacement therapy, comprising administering an effective amount of the steroid of claim 1.

* * * * *